United States Patent
Weadock et al.

(10) Patent No.: US 9,119,606 B2
(45) Date of Patent: Sep. 1, 2015

(54) SEALANT DELIVERY DEVICE FOR ANASTOMOTIC STAPLER

(71) Applicant: Ethicon, Inc., Somerville, NJ (US)

(72) Inventors: Kevin Weadock, Hillsborough, NJ (US); Kevin D. Trangone, Parsippany, NJ (US); Leo B. Kriksunov, Ithaca, NY (US); Robert J. Tannhauser, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 363 days.

(21) Appl. No.: 13/745,948

(22) Filed: Jan. 21, 2013

(65) Prior Publication Data

US 2014/0207186 A1 Jul. 24, 2014

(51) Int. Cl.
*A61B 17/00* (2006.01)
*A61B 17/115* (2006.01)

(52) U.S. Cl.
CPC ....... *A61B 17/00491* (2013.01); *A61B 17/1155* (2013.01); *A61B 2017/00495* (2013.01)

(58) Field of Classification Search
None
See application file for complete search history.

(56) References Cited

U.S. PATENT DOCUMENTS

| | | | |
|---|---|---|---|
| 5,271,544 A | 12/1993 | Fox | |
| 6,352,710 B2 | 3/2002 | Sawhney | |
| 6,652,542 B2 | 11/2003 | Blatter | |
| 6,758,219 B2 | 7/2004 | Sapala | |
| 7,517,356 B2 | 4/2009 | Heinrich | |
| 7,717,313 B2 | 5/2010 | Criscuolo | |
| 7,744,624 B2 | 6/2010 | Bettuchi | |
| 7,823,592 B2 | 11/2010 | Bettuchi | |
| 7,922,743 B2 * | 4/2011 | Heinrich et al. | 606/219 |
| 7,938,307 B2 | 5/2011 | Bettuchi | |
| 7,951,166 B2 | 5/2011 | Orban, III | |
| 7,972,357 B2 | 7/2011 | Bettuchi | |
| 8,096,458 B2 | 1/2012 | Hessler | |
| 8,118,206 B2 | 2/2012 | Zand | |
| 8,123,766 B2 | 2/2012 | Bauman | |
| 8,146,791 B2 | 4/2012 | Bettuchi | |
| 8,167,895 B2 | 5/2012 | D'Agostino | |
| 8,241,308 B2 | 8/2012 | Kortenbach | |
| 8,281,975 B2 | 10/2012 | Criscuolo | |
| 2002/0165541 A1 | 11/2002 | Whitman | |
| 2002/0185517 A1 | 12/2002 | Vresh | |

(Continued)

FOREIGN PATENT DOCUMENTS

EP 1647231 A1 4/2006
EP 1804685 7/2007

(Continued)

OTHER PUBLICATIONS

Liu CD, Glantz GJ, Livingston EH. Fibrin glue as a sealant for high-risk anastomosis in surgery for morbid obesity. Obes Surg. 2003;13:45-48.

(Continued)

*Primary Examiner* — Tuan V Nguyen
(74) *Attorney, Agent, or Firm* — David R. Crichton; Leo Kriksunov

(57) ABSTRACT

The present invention relates to surgical instruments and a method for applying an adhesive or sealant to an anastomosis site immediately prior and/or during anastomotic surgical stapling. The present invention further relates to surgical instruments, devices, and methods for applying sealant to a target tissue of a surgical site being anastomotically joined so as to prevent leakage.

15 Claims, 10 Drawing Sheets

(56) References Cited

U.S. PATENT DOCUMENTS

| | | |
|---|---|---|
| 2003/0108588 A1 | 6/2003 | Chen |
| 2003/0109899 A1 | 6/2003 | Fisher |
| 2003/0139771 A1 | 7/2003 | Fisher |
| 2003/0158598 A1 | 8/2003 | Ashton |
| 2004/0045562 A1 | 3/2004 | Sapala |
| 2004/0077648 A1 | 4/2004 | Timmer |
| 2005/0184121 A1 | 8/2005 | Heinrich |
| 2006/0085031 A1 | 4/2006 | Bettuchi |
| 2006/0085032 A1 | 4/2006 | Viola |
| 2006/0085033 A1 | 4/2006 | Criscuolo |
| 2006/0085034 A1 | 4/2006 | Bettuchi |
| 2006/0085036 A1 | 4/2006 | Viola |
| 2006/0108393 A1 | 5/2006 | Heinrich |
| 2006/0135992 A1 | 6/2006 | Bettuchi |
| 2006/0142736 A1 | 6/2006 | Hissink |
| 2007/0027473 A1 | 2/2007 | Vresh |
| 2007/0048251 A1 | 3/2007 | Arthur |
| 2008/0027472 A1 | 1/2008 | Nielsen |
| 2008/0110959 A1 | 5/2008 | Orban |
| 2008/0125811 A1 | 5/2008 | Bettuchi |
| 2008/0132923 A1 | 6/2008 | Fowler |
| 2008/0161907 A1 | 7/2008 | Chen |
| 2008/0255650 A1 | 10/2008 | Kelley |
| 2008/0283577 A1 | 11/2008 | Boyden |
| 2008/0287878 A1 | 11/2008 | Tanaka |
| 2009/0068247 A1 | 3/2009 | Jay |
| 2009/0270887 A1 | 10/2009 | Meagher |
| 2009/0281559 A1 | 11/2009 | Swain |
| 2010/0204728 A1 | 8/2010 | Bettuchi |
| 2010/0264195 A1 | 10/2010 | Bettuchi |
| 2010/0268022 A1 | 10/2010 | Thompson |
| 2010/0282815 A1 | 11/2010 | Bettuchi |
| 2010/0294826 A1 | 11/2010 | Boyden |
| 2011/0024476 A1 | 2/2011 | Bettuchi |
| 2011/0024481 A1 | 2/2011 | Bettuchi |
| 2011/0036894 A1 | 2/2011 | Bettuchi |
| 2011/0139853 A1 | 6/2011 | Viola |
| 2011/0147432 A1 | 6/2011 | Heinrich |
| 2011/0238097 A1 | 9/2011 | Bettuchi |
| 2012/0018487 A1 | 1/2012 | Bettuchi |
| 2012/0165922 A1 | 6/2012 | Gong |

FOREIGN PATENT DOCUMENTS

| | | |
|---|---|---|
| EP | 1804681 B1 | 8/2007 |
| EP | 1929958 A2 | 6/2008 |
| EP | 1652481 B1 | 6/2009 |
| EP | 1647230 B1 | 11/2009 |
| EP | 1825821 B1 | 9/2010 |
| EP | 1556097 B1 | 8/2011 |
| EP | 2366335 A2 | 9/2011 |
| EP | 2404555 A2 | 1/2012 |
| EP | 1381321 B1 | 4/2012 |
| JP | 2007229457 A | 9/2007 |
| JP | 2011235134 | 11/2011 |
| JP | 2011251156 A | 12/2011 |
| WO | WO 03088845 A2 | 10/2003 |
| WO | WO2004039424 A1 | 5/2004 |
| WO | WO2006044490 A2 | 4/2006 |
| WO | WO 2006044799 A2 | 4/2006 |
| WO | WO2006044800 A2 | 4/2006 |
| WO | WO2006108050 A2 | 10/2006 |
| WO | WO2008124638 A1 | 10/2008 |
| WO | WO2008140989 A2 | 11/2008 |
| WO | WO2009115992 A2 | 9/2009 |
| WO | WO 2009153748 A9 | 12/2009 |
| WO | WO 2012027320 A2 | 3/2012 |

OTHER PUBLICATIONS

Lee MG, Provost DA, Jones DB. Use of fibrin sealant in laparoscopic gastric bypass for the morbidly obese. Obes Surg. 2004;14:1321-1326.

Papavramidis ST, Eleftheriadis EE, Papavramidis TS, et al. Endoscopic management of gastrocutaneous fistula after bariatric surgery by using a fibrin sealant. Gastrointest Endosc. 2004;59:296-300.

Garcia-Caballero M, Carbajo M, Martinez-Moreno JM, et al. Drain erosion and gastro-jejunal fistula after one-anastomosis gastric bypass: endoscopic occlusion by fibrin sealant. Obes Surg. 2005;15:719-722.

Sapala JA, Wood MH, Schuhknecht MP. Anastomotic leak prophylaxis using a vapor-heated fibrin sealant: report on 738 gastric bypass patients. Obes. Surg. 2004;14:35-42.

Silecchia G, Boru CE, Mouiel J, et al. Clinical evaluation of fibrin glue in the prevention of anastomotic leak and internal hernia after laparoscopic gastric bypass: preliminary results of a prospective, randomized multicenter trial.Obes Surg. 2006;16:125-131.

Silecchia G, Boru CE, Mouiel J, et al. The use of fibrin sealant to prevent major complications following laparoscopic gastric bypass: results of a multicenter, randomized trial. Surg Endosc. 2008;22:2492-2497.

US 8,152,042, 04/2012, Bettuchi (withdrawn)

\* cited by examiner

SEALANT DELIVERY DEVICE FOR ANASTOMOTIC STAPLER

FIELD OF THE INVENTION

The present disclosure relates to surgical instruments and methods for enhancing properties of tissue repaired or joined by surgical staples and, more particularly to surgical instruments and methods designed to apply a non-mechanical biocompatible wound closure material to enhance the properties of repaired or adjoined tissue at a target surgical site, especially when sealing an anastomosis between adjacent intestinal sections.

BACKGROUND OF THE INVENTION

Throughout the years the medical field has utilized various techniques in an effort to join or bond body tissue together. Historically, suturing was the accepted technique for rejoining severed tissues and closing wounds. Suturing was historically achieved with a surgical needle and a suturing thread, and more recently, with a variety of polymeric or metallic staples. The intended function of sutures is to hold the edges of a wound or tissue against one another during the healing process so as to reduce discomfort, pain, scarring and the time required for healing. Staples have recently been used to replace suturing when joining or anastomosing various body structures, such as, for example, the bowel. The surgical stapling devices employed to apply these staples are generally designed to simultaneously cut and seal an extended segment of tissue in a patient.

Linear or annular surgical stapling devices are employed by surgeons to sequentially or simultaneously apply one or more rows of surgical fasteners, e.g., staples or two-part fasteners, to body tissue for the purpose of joining segments of body tissue together and/or for the creation of an anastomosis. Linear surgical stapling devices generally include a pair of jaws or finger-like structures between which body tissue to be joined is placed. When the surgical stapling device is actuated and/or "fired," firing bars move longitudinally and contact staple drive members in one of the jaws, and surgical staples are pushed through the body tissue and into and against an anvil in the opposite jaw thereby crimping the staples closed. A knife blade may be provided to cut between the rows/lines of staples.

Annular surgical stapling devices generally include an annular staple cartridge assembly including a plurality of annular rows of staples (typically two), an anvil assembly operatively associated with the annular cartridge assembly, and an annular blade disposed internal of the rows of staples. In general, an end-to-end anastomosis stapler typically places an array of staples into the approximated sections of a patient's bowels or other tubular organs. The resulting anastomosis contains an inverted section of bowel which contains numerous "B" shaped staples to maintain a secure connection between the approximated sections of bowel.

Anastomotic leaks may result in significant morbidity and frequently death. In addition to the use of surgical staples, sealants, e.g., synthetic or biological sealants, can be applied to the surgical site to guard against leakage. The biological sealants are typically applied to the outer surface of the anastomosis by using a dual lumen syringe or spray nozzle in a separate step. Still, the delivery of the sealant is compromised by an inability to get it at or between individual staple sites, and along staple lines and tissue seams. Typically, the biological sealants are manually applied to the outer surface of the staple line by a physician by spraying on, brushing on, swabbing on, or any combinations thereof. This manual application of biological sealant can lead to non-uniformity of the thickness of sealant across the staple line and/or omitting a portion of the intended coverage area due to inability to see or reach the desired location. In addition the manual application of the sealant is difficult to perform uniformly and efficiently, particularly because the sealants are designed to cure very quickly.

The biological sealants are known to be applied to the outer surface of the anastomosis by using a dual lumen syringe or spray nozzle in a separate step. The efficacy of fibrin sealant in prevention of leak after bariatric surgery has been shown in nonrandomized studies, as shown in the following references:

Liu C D, Glantz G J, Livingston E H. Fibrin glue as a sealant for high-risk anastomosis in surgery for morbid obesity. Obes Surg. 2003; 13:45-48.

Lee M G, Provost D A, Jones D B. Use of fibrin sealant in laparoscopic gastric bypass for the morbidly obese. Obes Surg. 2004; 14:1321-1326.

Papavramidis S T, Eleftheriadis E E, Papavramidis T S, et al. Endoscopic management of gastrocutaneous fistula after bariatric surgery by using a fibrin sealant. Gastrointest Endosc. 2004; 59:296-300.

Garcia-Caballero M, Carbajo M, Martinez-Moreno J M, et al. Drain erosion and gastro-jejunal fistula after one-anastomosis gastric bypass: endoscopic occlusion by fibrin sealant. Obes Surg. 2005; 15:719-722.

Sapala J A, Wood M H, Schuhknecht M P. Anastomotic leak prophylaxis using a vapor-heated fibrin sealant: report on 738 gastric bypass patients. Obes. Surg. 2004; 14:35-42.

However, prospective, randomized, multicenter, clinical trials in laparoscopic bypass surgery (not lower anterior resection or sigmoidectomy) have shown that there was little difference in leak rates between fibrin glue and control groups, as shown in the below references:

Silecchia G, Boru C E, Mouiel J, et al. Clinical evaluation of fibrin glue in the prevention of anastomotic leak and internal hernia after laparoscopic gastric bypass: preliminary results of a prospective, randomized multicenter trial. Obes Surg. 2006; 16:125-131.

Silecchia G, Boru C E, Mouiel J, et al. The use of fibrin sealant to prevent major complications following laparoscopic gastric bypass: results of a multicenter, randomized trial. Surg Endosc. 2008; 22:2492-2497.

One possible underlying reason for the poor performance of the sealant is that the delivery of the sealant is not optimized or is compromised by an inability to get it at or between individual staple sites, and along staple lines and tissue seams.

U.S. Pat. No. 8,281,975, entitled "Surgical apparatus and structure for applying sprayable wound treatment material" to Criscuolo and Bettuchi, discloses an apparatus for forming an anastomosis between adjacent sections of tissue. The apparatus includes a body portion; an actuation assembly operatively supported at a proximal end of the body portion; an anvil assembly movably mounted at the distal end of the body portion for movement toward and away from the body portion; an approximation assembly extending between the body portion and the anvil assembly for moving the anvil toward and away from the tubular body portion; a dispersion assembly operatively associated with the approximation assembly, the dispersion assembly including at least one angled surface defining at least one channel interposed between the anvil assembly and the body portion and being configured to dispense a fluid therefrom; and at least one conduit for conducting wound treatment material to the dispersion assembly.

The disadvantages of the Criscuolo apparatus relate to the conduit and the dispersion assembly being built into the body of the apparatus. Thus, the system can be clogged with tissue, blood, body fluids, and other matter during the installation of the apparatus within the intestine in preparation to the circular anastomosis, and thereby rendering the apparatus incapable of the delivery of the sealant as intended. Moreover, if the dispersion assembly exit nozzles became clogged by the rapidly curing sealant, for instance due to the minor delay or complication during the anastomotic procedure, the delivery of the sealant will be prevented with no recourse. In addition, the sterilization and cleaning of the apparatus becomes complicated once a rapidly curing sealant is introduced into the narrow channels and orifices of the conduit and the dispersion assembly. Further, the size of the dispersion assembly is fixed by the size of the approximation assembly on which it is formed and thus the dispersion assembly cannot be readily adjusted or adapted for different spraying pattern, spray coverage, and the like to accommodate different anatomy of the patient and different needs of the surgeon performing the anastomosis.

U.S. Pat. No. 8,152,042 discloses a number of embodiments for improving sealing at the anastomotic site. In some embodiments, a washer or structural body is wrapped completely around the anvil shaft, with staples driven through the structural body to release the sealant.

U.S. Pat. No. 7,972,357 to Bettuchi and entitled "Extraluminal sealant applicator and method" and U.S. Pat. No. 7,744,624 disclose apparatus for applying sealant to a target tissue of a surgical site. The apparatus includes a handle, a conduit and an end effector. The handle has means configured and adapted for operating the end effector and dispensing biological sealant to the surgical site via the end effector. The conduit stores and/or carries sealant towards the end effector. The end effector is configured to clamp around a body organ or tissue and apply and confine biological sealant in a substantially uniform manner. More specifically, the references disclose a system for applying sealant to a target tissue of a surgical site, comprising: a two-part sealant comprising a first part and a second part; an apparatus comprising: a handle; an end effector in operative association with the handle, the end effector including a first jaw member, a second jaw member, and a sealant-applying structure configured for applying sealant to the target tissue; the first jaw member being in fluid communication with a first conduit and a second conduit to convey sealant to the sealant-applying structure; the second jaw member being in fluid communication with a third conduit and a fourth conduit to convey sealant to the sealant-applying structure; the first and third conduits configured for conveying the first part of the two-part sealant to the sealant-applying structure; and the second and fourth conduits configured for conveying the second part of the two-part sealant to the sealant-applying structure. The Bettuchi apparatus is bulky and is only capable of applying the sealant on the outside and around the tissue joint, with additional difficulty in precisely targeting the application of the sealant.

U.S. Pat. No. 8,096,458 entitled "Pouch used to deliver medication when ruptured" describes a surgical stapling device, comprising: a handle portion; an elongate body portion; and a head portion located at the distal end of the body portion, the head portion including an anvil assembly, a staple cartridge assembly and a knife blade, the staple cartridge assembly having an annular array of staples, the anvil assembly being connected to the body portion along a shaft, the anvil assembly including: an anvil plate defining a plurality of staple forming pockets therein and a recess; and a wound treatment material disposed substantially within the recess.

U.S. Pat. No. 8,241,308 entitled "Tissue fastening devices and processes that promote tissue adhesion" discloses a fastener for fastening tissue segments having tissue surfaces, the fastener comprising: a first fastener member defining a fluid opening configured to receive a therapeutic agent, a plurality of fluid ports configured to deliver the therapeutic agent to the tissue segments, and a passageway between the fluid opening and the plurality of fluid ports; and a second fastener member having a substantially flat base and a post extending from the base proximate a center of the base, the post defining an opening for receiving and retaining the first fastener member such that the tissue segments to be fastened are retained between the first and second fastening members, the substantially flat base extending radially beyond a periphery of the post; wherein a longitudinal axis extends through the fluid opening, the fluid ports being radially arranged about the axis.

SUMMARY OF THE INVENTION

The present invention relates to surgical instruments and a method for applying an adhesive or sealant to an anastomosis site immediately prior and/or during anastomotic surgical stapling. The present invention further relates to surgical instruments, devices, and methods for applying sealant to a target tissue of a surgical site being anastomotically joined so as to prevent leakage. As used herein, sealant is intended to encompass a broad range of biologically compatible materials including tissue adhesives, tissue sealing compositions, etc.

The present invention, in one embodiment, relates to a device for applying a two part adhesive or sealant to an anastomosis site prior to stapling with a circular anastomosis surgical stapling instrument, the device having a hollow housing having a top surface and an opposing bottom surface with at least two separate channels within said housing, a plurality of nozzles disposed circumferentially on the top surface and on the bottom surface with the nozzles in fluid communication with the channels, a manifold connector attached to the housing, the connector being in fluid communication with the channels and adapted to be connected to a dual lumen cannula supplying sealant components, and a coupler adapted to mount the device to the circular anastomosis surgical stapling instrument. The coupler can be adapted to mount the device to a shaft between an anvil and a stapling head of the circular anastomosis surgical stapling instrument. The housing can have a generally a semicircular shape, with a housing gap dividing the housing into two housing arms.

The present invention, in another embodiment, relates to a method of performing anastomosis by preparing the anastomosis site for performing anastomotic stapling, connecting the manifold connector described above to a multi-lumen cannula, preferably dual lumen cannula, coupling the device to the shaft of circular anastomosis surgical stapling instrument between the anvil and the stapling head of the circular anastomosis surgical stapling instrument, connecting the dual lumen cannula to the source of a two part sealant, delivering the two part sealant from the source via the dual lumen cannula into the device, ejecting the two part sealant from the nozzles, depositing the two part sealant onto the anastomosis site, removing the device from the shaft, firing the circular anastomosis surgical stapling instrument delivering staples and performing anastomosis.

DETAILED DESCRIPTION OF THE INVENTION

Figure 1:
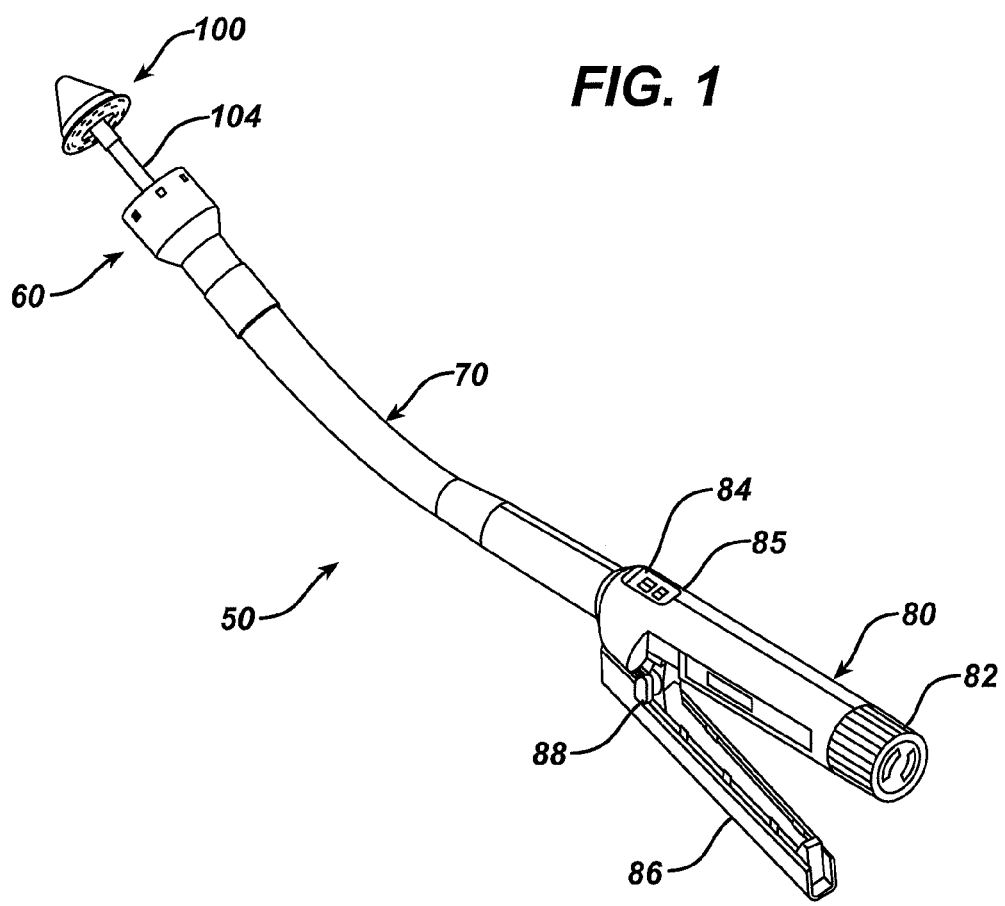
FIG. 1 shows a prospective view of a surgical anastomosis stapling instrument or stapling device for performing a circular anastomosis stapling operation.

Referring now to FIG. 1, a generic surgical anastomosis stapling instrument or stapling device for performing a circular anastomosis stapling operation is shown, with the figure taken from the U.S. Pat. No. 5,271,544 "Surgical anastomosis stapling instrument", assigned to Ethicon, Inc., Somerville, N.J., and incorporated herein by reference in its entirety for all purposes. Various modifications and iterations of the shown stapling device are known in the art, having similar features. The circular anastomosis surgical stapling instrument 50 includes a distal stapling head assembly 60 connected by a longitudinally curved support shaft assembly 70 to a proximal actuator handle assembly 80. The stapling instrument includes an anvil assembly or anvil 100 which is slidable longitudinally relative to the stapling head assembly 60 and mounted on an axially extending moveable shaft 104. An optional rotatable adjusting knob 82 is provided at the proximal end of the actuator handle assembly 80 for adjusting the spacing between the stapling head assembly 60 and the anvil assembly 100. An optional movable indicator 84 is visible through an optional window 85 on top of the handle assembly 80 to indicate the staple height selected by rotation of the adjusting knob 82. The indicator 84 is movable indicating that the anvil gap is within a desired operating range of the stapling instrument 50. The position of the indicator 84 also indicates whether the selected staple height is large or small.

A staple actuating lever 86 is pivotally mounted on the actuator handle assembly 80 for driving the surgical staples from the stapling head assembly 60 when the anvil assembly 100 is closed to provide the desired staple height. A pivotal latching member 88 is mounted on the handle assembly 80 for locking the staple actuating lever 86 against movement to preclude actuation of the stapling head assembly 60 when the anvil gap is outside of a predetermined range.

The anastomosis can be performed by a variety of techniques known in the art. In one exemplary technique, low anastomosis of colon to rectum using the anastomotic stapler is performed. Briefly, and referring to FIGS. 2 and 3A, after stapler 50 is inserted through the anus (not shown), the descending colon 210 is fixated around anvil 100 with purse string sutures tied around the shaft 104 and the rectal stump 220 is fixated around stapling head 60 with purse string sutures also tied around the shaft 104 resulting in the assembly shown in FIGS. 2 and 3A-C. Anvil 100 is then pulled towards stapling head 60 as schematically shown in FIG. 3B, and then the staples 90 are deployed to join the tissue of the descending colon 210 and rectal stump 220 at their respective serosal surfaces, with simultaneous action of circular scalpel (not shown) within the stapler cutting away excessive tissue (inverted bowel) closest to shaft 104, resulting in anastomosis as shown in FIG. 3C. Stapler 50 is then removed resulting in anastomotic joint as shown in FIG. 3D. The diameter of the shaft 104 is shown schematically in FIG. 3D by arrows.

Figure 4A:
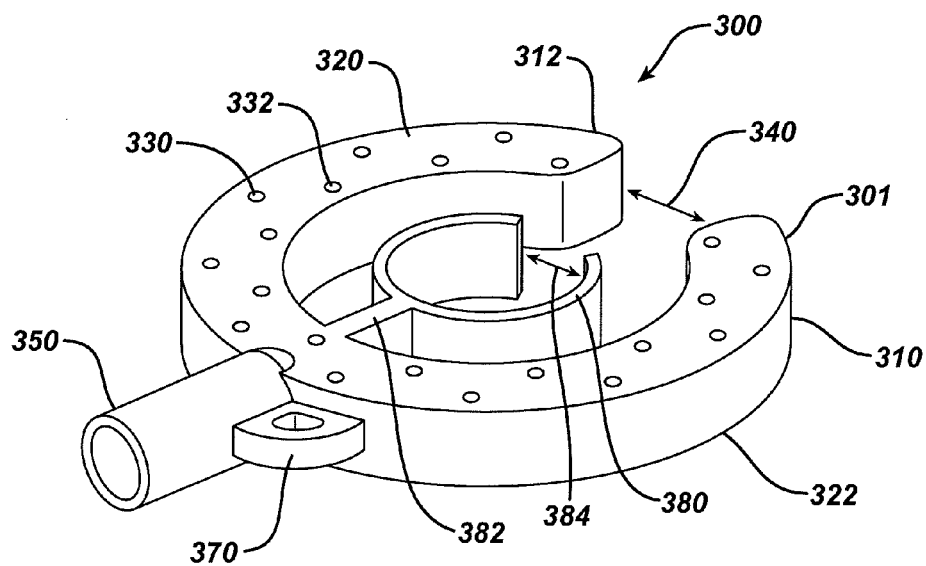
FIG. 4A shows a prospective top view.
Figure 4B:
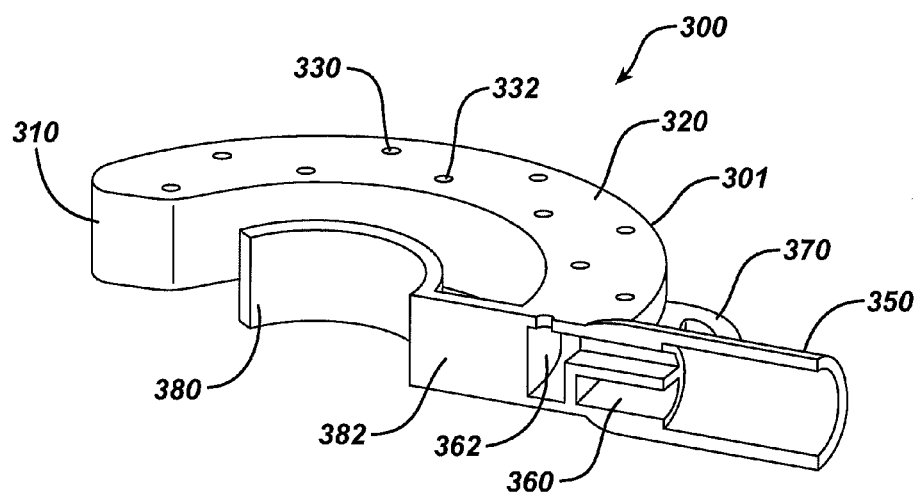
FIG. 4B shows a cross-sectional top view of embodiments of the present invention.
Figure 4C:
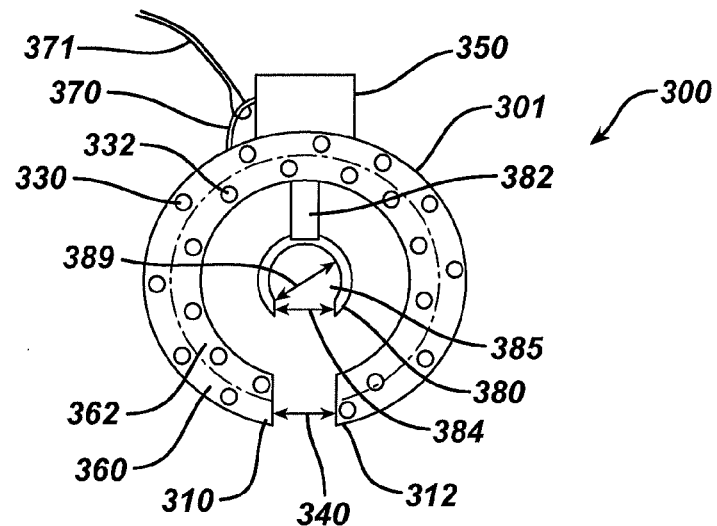
FIGS. 4C and 4D show top views of the present invention.
Figure 4D:
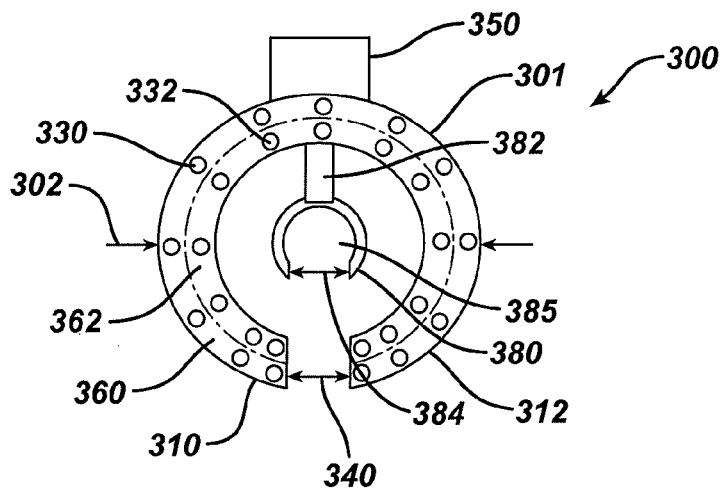

Referring now to FIG. 4A showing a prospective view, FIG. 4B showing a prospective cross-sectional view, and FIGS. 4C-D showing schematic top view of embodiments of the present invention, a sealant delivery device 300 comprises a hollow housing 301 having in one embodiment a semicircular or open circle or horseshoe shape of diameter 302 (diameter 302 is shown in FIG. 4D) with a housing gap 340 separating semicircular arms 310 and 312 having top surface 320 and opposing bottom surface 322. Other shapes of hollow housing 301 are contemplated, including square, hexagon, polygon, ellipse, and other shapes. Top surface 320 and/or optionally bottom surface 322 as well have arrays of circumferentially oriented exit openings, such as exit apertures, ejection ports, or nozzles 330 and 332 for spraying or ejecting sealant upwards from top surface 320 and optionally downwards from bottom surface 322, either perpendicularly or under angle to top surface 320 and bottom surface 322. Nozzles 330 and 332 comprise passages connecting channels 360 and 362 to top surface 320 and opposing bottom surface 322. In certain embodiments nozzles 330 and 332 are represented by vias formed in top surface 320 and bottom surface 322 perpendicularly or under angle to top surface 320 and bottom surface 322 and providing connection of channels 360 and 362 to surfaces of housing 301. In a preferred embodiment, first component nozzles 330 are used to deliver a first component of a two-part sealant, and second component nozzles 332 are used to deliver a second component of the two-part sealant, with both components sprayed simultaneously, mixing at or near the serosal surfaces. No mixing of components of the two-part sealant occurs inside sealant delivery device 300. In one embodiment, nozzles 330 and 332 are all positioned only on one surface of hollow housing 301, such as only on top surface 320 or only on bottom surface 322.

A manifold connector 350, either integrally formed on housing 301 or attached to housing 301 is adapted to be connected to the sealant components supply line, with two separate conduits or channels 360 and 362 running within housing 301 inside and along circular or semicircular arms 310 and 312 and having an entrance inside manifold connector 350. Channels 360 and 362 are in fluid communication with nozzles 330 and 332 respectively but are completely separated from each other within housing 301. In one embodiment, nozzles 330 and 332 are positioned in an interdigitated arrangement along the circumference of arms 310 and 312 as shown in FIGS. 4A-4C, with nozzle 330 for the first component followed along the circumference with nozzle 332 for the second component and so on. In another embodiment, nozzles 330 and 332 are positioned in an arrangement shown in FIG. 4D wherein pairs of nozzles 330 and 332 are positioned at the approximately same angular locations around the circumference of arms 310 and 312.

Other ways of positioning of nozzles 330 and 332 around the circumference of arms 310 and 312 providing for a good mixing and good coverage of the serosal surfaces are possible, such as, for instance, two nozzles 330 followed by one nozzle 332, etc. (not shown).

Figure 4E:
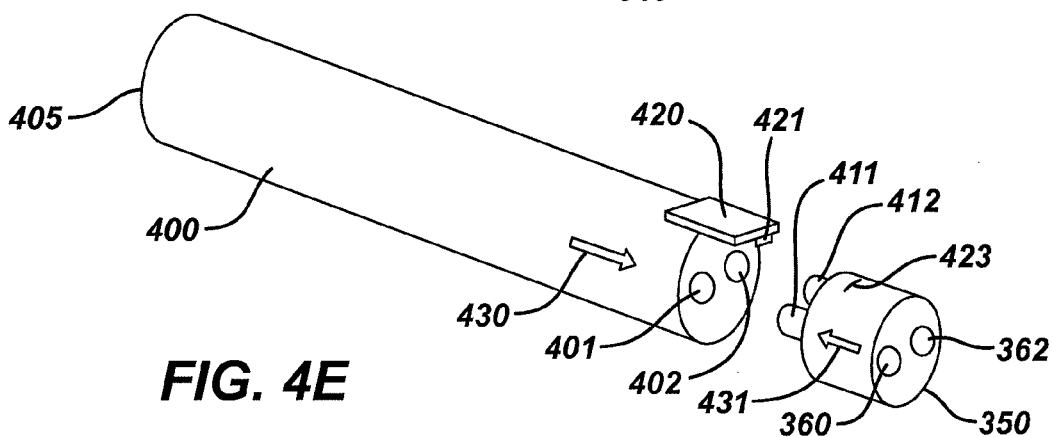
FIG. 4E shows a dual lumen embodiment.

A flexible dual lumen conduit or cannula 400, with one embodiment schematically shown in FIG. 4E, having at least two or optionally more than two lumens 401 and 402 can be connected to manifold connector 350 providing supply of first component of the two-part sealant to channel 360 and of second component of the two-part sealant to channel 362 without mixing of the components within sealant delivery device 300 (not shown in FIG. 4E). Optionally protruding connectors 411 and 412 (having a circular, semi-circular, rectangular, or any other appropriate shape to match up with the channels 360 and 362 having corresponding and matching shape) on manifold connector 350 provide a liquid tight seal and connection between lumens 401 and 402 of dual lumen cannula 400 and channels 360 and 362 of sealant delivery device 300. Dual lumen cannula 400 can be further coupled at the distal end 405 to a source of two-part sealant, such as a two-barrel syringe (not shown).

An optional locking feature 420 can be provided on dual lumen cannula 400 with a protrusion 421 adapted to fit into slot 423 on manifold connector 350. Locking feature 420 enables establishing locked connection of dual lumen cannula 400 to sealant delivery device 300 in registration of channels 360 and 362 connected to lumens 401 and 402 via protruding connectors 411 and 412. Other designs of locking feature 420 are possible and easily designed by a person skilled in the art. In another embodiment protruding connectors 411 and 412 have different sizes and/or shapes uniquely mating to lumens 401 and 402 resulting in connection of dual lumen cannula 400 to manifold connector 350 only possible with mating corresponding protruding connector to corresponding lumens, such as connector 411 to lumen 401 and connector 412 to lumen 402. In one embodiment, connector 411 and lumen 401 have circular cross-section, while connector 412 and lumen 402 have square cross-section. In one embodiment, markings such as arrows 430 and 431 are positioned on dual lumen cannula 400 and manifold connector 350 to facilitate connecting dual lumen cannula 400 to manifold connector 350 in registration.

An optional connector 370 is positioned on sealant delivery device 300. A tether 371 (shown in FIG. 4C) such as a lanyard, suture, or any flexible string, can be used so that the device can be easily removed after delivering the solutions of first component and second component of the two-part sealant (such as fibrinogen and thrombin) and just prior to firing the stapler.

In some embodiments, to provide for a better coverage of the area corresponding to housing gap 340 separating semicircular arms 310 and 312, higher density of nozzles is provided in the areas immediately close to housing gap 340, as shown in FIG. 4D.

As illustrated in FIGS. 4A-D, a coupler 382 is positioned substantially at the center of sealant delivery device 300. Coupler 382 is adapted to enable removable positioning of sealant delivery device 300 onto shaft 104 in the area between serosal surfaces which are about to be joined together by stapling, said area generally indicated by horizontal arrows on FIG. 2 and FIG. 3A. In some embodiments, coupler 382 has a generally semicircular or horseshoe shape formed by arms 380 separated by a coupler gap 384 with internal diameter 389 of coupler opening 385 in the coupler 382 substantially equal or smaller by 0.1-20% than the diameter of shaft 104. Coupler 382 can be quickly snappably affixed or locked onto and when needed removed from shaft 104. In one embodiment internal diameter 389 of coupler opening 385 is equal to diameter of shaft 104.

Coupler gap 384 has the dimensions to enable removable positioning of sealant delivery device 300 onto shaft 104. In some embodiments, the dimension of coupler gap 384 is selected to enable sealant delivery device 300 to be snappably affixed or locked onto and when needed removed from shaft 104. In some embodiments, the dimension of coupler gap 384 is equal to diameter of shaft 104, or smaller than the diameter of shaft 104 by 1% to 50%. In one embodiment, the dimension of coupler gap 384 is equal to 70% or 90% the diameter of shaft 104. In some embodiments, coupler arms 380 are flexible enough to accommodate passing of shaft 104 through coupler gap 384 when positioning sealant delivery device 300 onto shaft 104 and when removing sealant delivery device 300 from shaft 104.

In some embodiments, housing gap 340 has the dimensions so as to enable easy passage of shaft 104 when affixing sealant delivery device 300 to shaft 104 and when removing sealant delivery device 300 from shaft 104. In some embodiments, the dimension of housing gap 340 is equal to diameter of shaft 104, or larger than the diameter of shaft 104 by 1% to 30%. In one embodiment, the dimension of housing gap 340 is equal to 110% of the diameter of shaft 104. In some embodiments, the dimension of housing gap 340 is smaller than the diameter of shaft 104 by 1% to 75%.

Figure 5A:
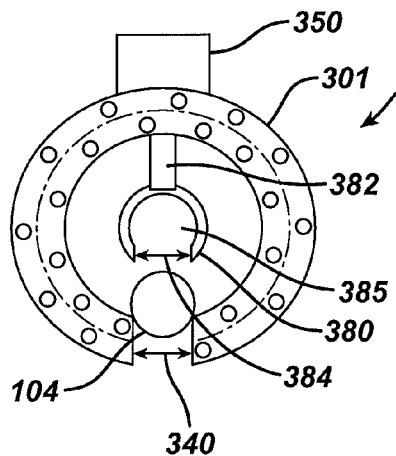
FIGS. 5A-5I show schematic top views of embodiments of the present invention and installation onto the anastomotic stapler.
Figure 5B:
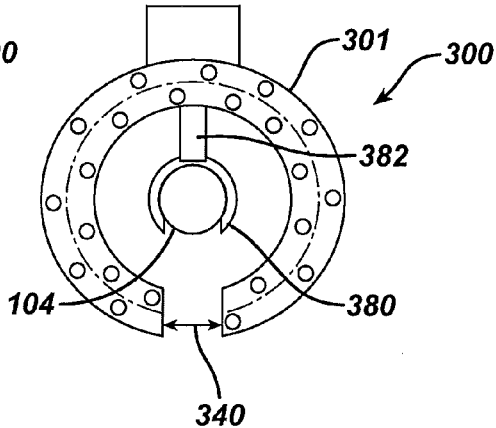

FIG. 5A shows installation of sealant delivery device 300 on shaft 104 with shaft 104 just past housing gap 340. FIG. 5B shows installation of sealant delivery device 300 on shaft 104 with shaft 104 passed through coupler gap 384 and is within coupler opening 385 snappably affixed to coupler 382.

Figure 5C:
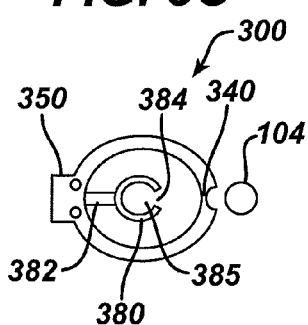
Figure 5D:
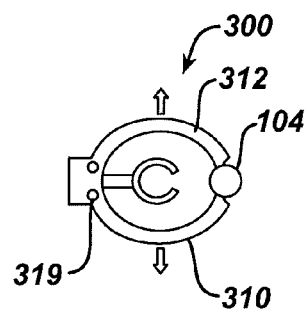
Figure 5E:
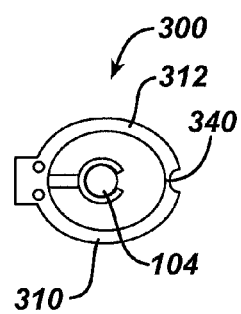

Referring now to FIG. 5C-5E, in some embodiments, housing gap 340 has the dimensions ranging from substantially zero to about 90% of the diameter of shaft 104. In such embodiments, arms 310 and 312 are sufficiently flexible or moveable on optional hinges 319 to open wide enough to accommodate passing of shaft 104 through housing gap 340 when positioning sealant delivery device 300 onto shaft 104 and when removing sealant delivery device 300 from shaft 104. FIG. 5C shows sealant delivery device 300 and shaft 104 prior to attaching; FIG. 5D shows sealant delivery device 300 being attached onto shaft 104 with arms 310 and 312 opening to at least the diameter of shaft 104 to accommodate passage of shaft 104; FIG. 5E shows sealant delivery device 300 fully attached to shaft 104 in position for sealant delivery with arms 310 and 312 fully closed and housing gap 340 very small or substantially zero. Advantageously, this embodiment enables full circular coverage of serosal surfaces with sealant due to very small housing gap 340. Nozzles 330 and 332 are not shown in FIGS. 5C-5E.

Figure 5F:
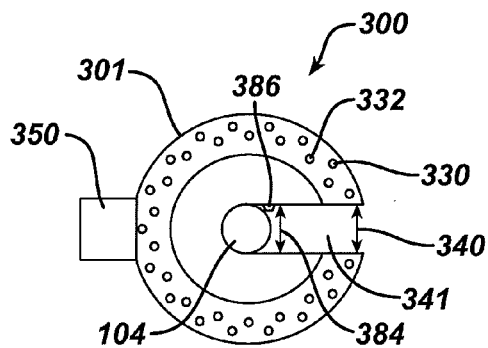

Referring now to FIG. 5F, an embodiment of the present invention is shown whereby coupler is integrated into sealant delivery device 300 as a radial cutout 341. In this embodiment, sealant delivery device 300 has housing 301 having polygonal, elliptical, disk, or any other shape, with shape of a disk shown in FIG. 5F, with a radial cutout 341 extending from periphery of housing 301 to the center of housing 301, with housing gap 340 transitioning into coupler gap 384 both having dimensions approximately equal to diameter of shaft 104. Optionally one or more locking elements 386 are provided to enable snappable attachment to shaft 104 and securement of shaft 104 in the center of device 300. Optional locking element 386 represents a small protrusion or bump within radial cutout 341, which requires additional force for shaft 104 to pass over during sealant delivery device 300 installation onto shaft 104 or removal from shaft 104. In certain embodiments there are 1 or 2 locking elements 386 which can have height from 0.1 to 2 mm, such as 0.5 mm.

Figure 5G:
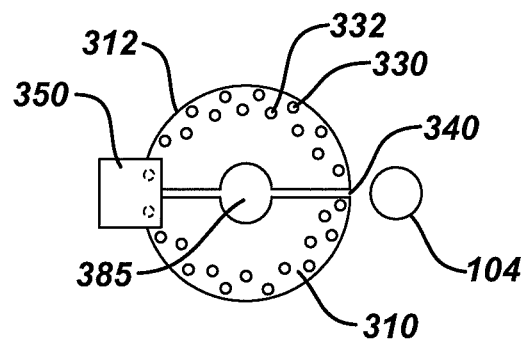
Figure 5H:
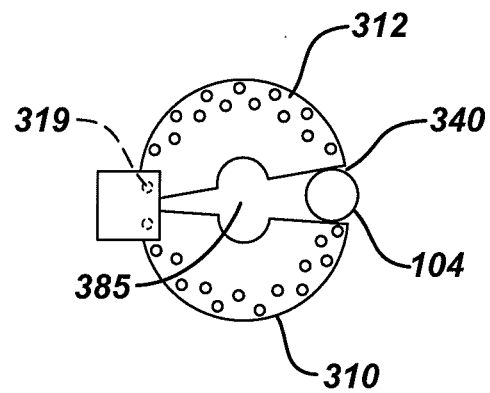
Figure 5I:
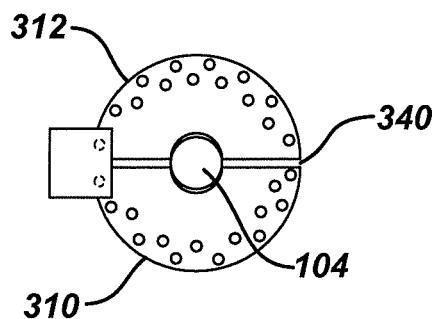

Referring now to FIGS. 5G-I, an embodiment of the present invention is shown whereby, similarly to embodiments 5C-E, housing gap 340 has the dimensions substantially close to zero, and similarly to embodiment 5F, coupler is integrated into sealant delivery device 300 as coupler opening 385 formed by semicircular cutouts in arms 310 and 312. In this embodiment, arms 310 and 312 are sufficiently moveable on optional hinges 319 providing enough flexibility to open wide enough to accommodate passing of shaft 104 through housing gap 340 when positioning sealant delivery device 300 onto shaft 104 and when removing sealant delivery device 300 from shaft 104. FIG. 5G shows sealant delivery device 300 and shaft 104 prior to attaching; FIG. 5H shows sealant delivery device 300 being attached onto shaft 104 with arms 310 and 312 opening to at least the diameter of shaft 104 to accommodate passage of shaft 104; FIG. 5I shows sealant delivery device 300 fully attached onto shaft 104 in position for sealant delivery with arms 310 and 312 fully closed and housing gap 340 very small or substantially zero. Advantageously, this embodiment enables full circular coverage of serosal surfaces with sealant due to very small housing gap 340.

Figure 2:
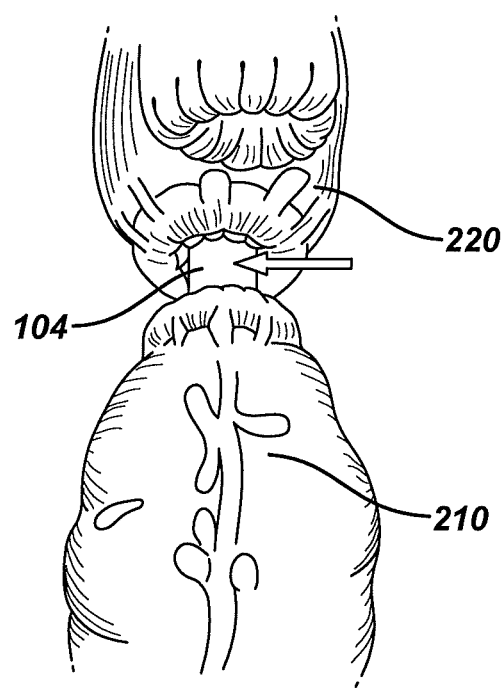
FIG. 2 shows schematic prospective view of one step during performing low anastomosis of colon to rectum using the anastomotic stapler.
Figure 3A:
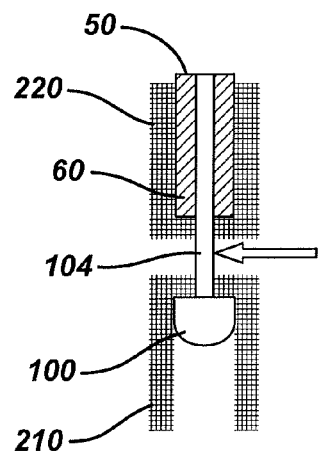
FIGS. 3A-3D shows schematic cross-sectional view of several steps during performing anastomosis using the anastomotic stapler.
Figure 3B:
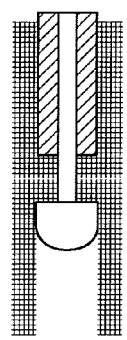
Figure 3C:
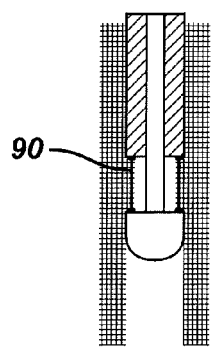
Figure 3D:
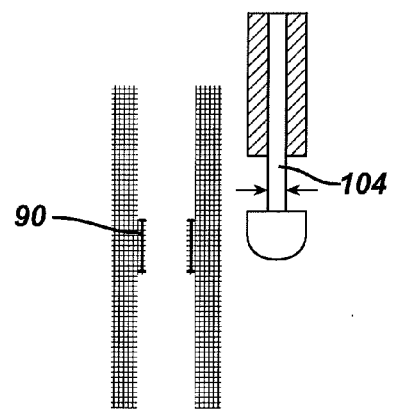
Figure 6A:
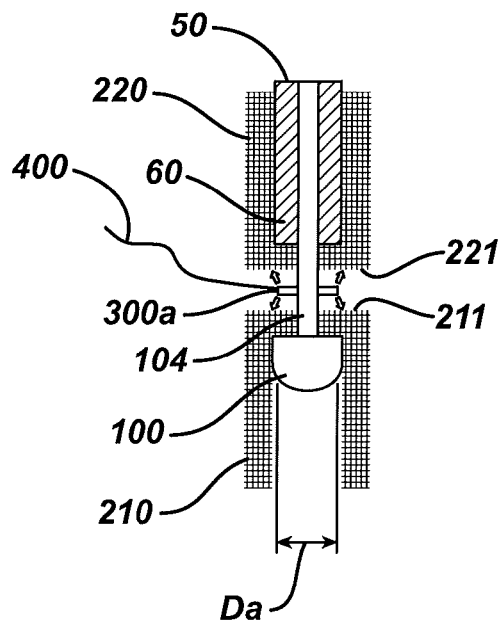
FIG. 6A-6C show schematic cross-sectional views of embodiments of the present invention in operation during anastomosis using the anastomotic stapler.
Figure 6B:
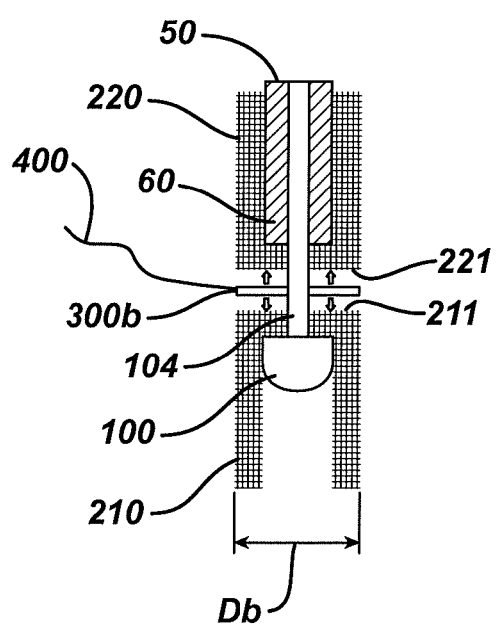
Figure 6C:
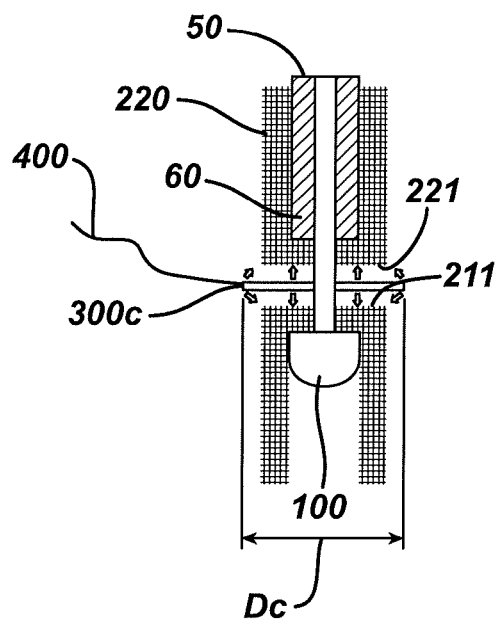

Referring now to FIG. 6, the positioning of sealant delivery device 300 onto shaft 104 in the area between serosal surfaces which are about to be stapled is further illustrated, with positioning being similar to the areas indicated by horizontal arrows on FIG. 2 and FIG. 3A. Referring to FIGS. 6A-6C, sealant delivery device 300a, 300b, and 300c is positioned on shaft 104 between serosal surfaces 211 and 221 which are about to be anastomotically stapled together as shown in sequences In FIGS. 3A-3D. Dual lumen cannula 400 is shown connected to sealant delivery device 300 for delivery of two part sealant. FIG. 6A shows sealant delivery device 300a having diameter Da smaller vs. the diameter of the tubular tissue structure (such as descending colon 210 and rectal stump 220), or alternatively similar to anvil 100 diameter. FIG. 6B shows sealant delivery device 300b having diameter Db about equal to the diameter of the tubular tissue structure (such as descending colon 210 and rectal stump 220), or larger than anvil 100 diameter. FIG. 6C shows sealant delivery device 300c having diameter Dc larger than the diameter of the tubular tissue structure (such as descending colon 210 and rectal stump 220), or alternatively much larger relative to anvil 100 diameter. The direction of the spray of the components of the two-part sealant from ejection ports or nozzles 332 and 330 (not shown) is schematically indicated by arrows.

For optimized coverage, in some embodiments nozzles are directing spray at 90 degrees or perpendicular to top surface 320 and bottom surface 322. In some embodiments, nozzles can direct spray at 45-80 degrees relative to top surface 320 and bottom surface 322, with the direction of spray towards serosal surfaces. As can be seen from schematic representation in FIG. 6, for optimal coverage, in some embodiments nozzles 332 and 330 are directed orthogonally to sealant delivery device 300 with sprays perpendicular to top surface 320 and bottom surface 322. In certain embodiments, nozzles 332 and 330 are directed angularly for better coverage.

Figure 7:
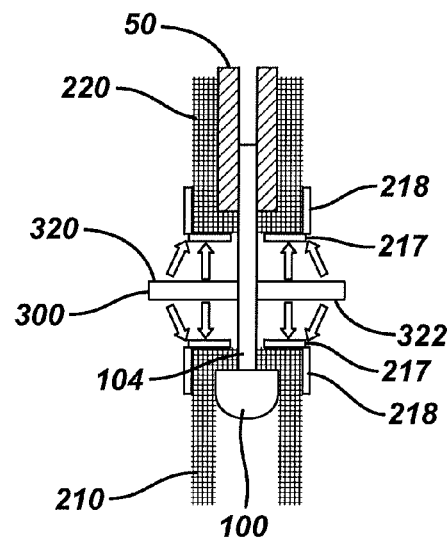
FIG. 7 shows schematic cross-sectional view of an embodiment of the present invention in operation during anastomosis using the anastomotic stapler.

Referring now to FIG. 7, the spray arrows directed substantially perpendicularly to top surface 320 and bottom surface 322 to show the spray coverage mostly to areas 217 i.e. to serosal surface about to be stapled together. The spray arrows directed angularly show that in this case the spray coverage is not limited to areas 217 but also covers areas 218 which are in immediate vicinity of the anastomosis. Advantageously, after stapling, sealant from areas 218 provides additional securement and sealing of the anastomotic joint, in addition to the sealant deposited in the areas 217.

In addition to the angular direction of nozzles as shown in FIG. 7, in some embodiments nozzles 332 and 330 are directed angularly for better overlap of deposition between first component and second component of sealant, so that the area onto which the first component spray is directed is also covered by the second component and vice versa (not shown in FIG. 7).

In some embodiments, nozzles 332 and 330 are made larger and/or denser as they go further from manifold 350 to make the spray more uniform to accommodate drop in pressure along arms 310 and 312. FIG. 8 shows higher density of nozzles 330, 332 in the proximity to housing gap 340, farthest away from manifold 350.

In one embodiment (not shown), nozzles 332 and 330 close to housing gap 340 are aimed angularly so that some spray also covers the area on serosal surfaces corresponding to housing gap 340 between arms 310 and 312.

In use, after the surgical site is ready for performing anastomotic stapling, for example after purse string sutures have been applied to the tubular segments and prior to stapling, sealant delivery device 300 is connected to dual lumen cannula 400 at manifold 350 and fixably positioned onto shaft 104, dual lumen cannula 400 is connected to the source of two part sealant, the two part sealant is delivered to sealant delivery device 300 and ejected or sprayed from nozzles 330 and 332 simultaneously or sequentially to the serosal surfaces which are about to be stapled together, such as, in one example, towards proximal colon and distal colon, or in another example, descending colon 210 and rectal stump 220, resulting in coating of the serosal surfaces. Sealant delivery device 300 is then removed from shaft 104 by pulling on dual lumen cannula 400 or by using lanyard or tether 371 attached to lanyard or tether connector 370. Surgical stapling instrument 50 is then fired delivering staples and performing anastomosis.

The two part sealant, such as for instance a sealant comprising fibrinogen and thrombin, is expected to cure or crosslink immediately before, during, and after firing of staples, with at least some curing and preferably most of the curing occurring after the deployment of staples. Timing of curing can be varied and changed according to the surgeons' preferences. Advantageously, during stapling, some sealant will be driven between individual staple sites, and along staple lines and tissue seams to fill remaining cavities, holes, non-uniformities, and pores, thus improving the quality of the seal and preventing anastomotic leaks.

Figure 8A:
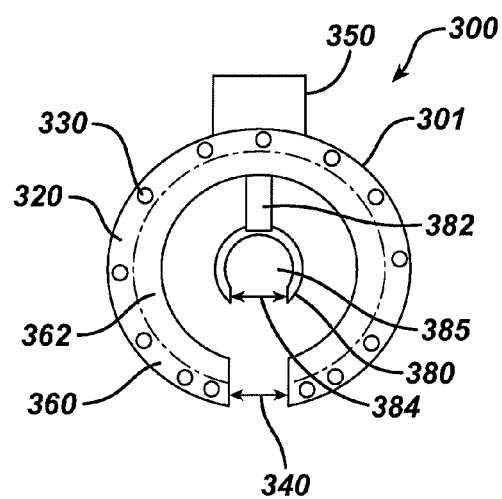
FIGS. 8A and 8B show schematic top and bottom views of an embodiment of the present invention.
Figure 8B:
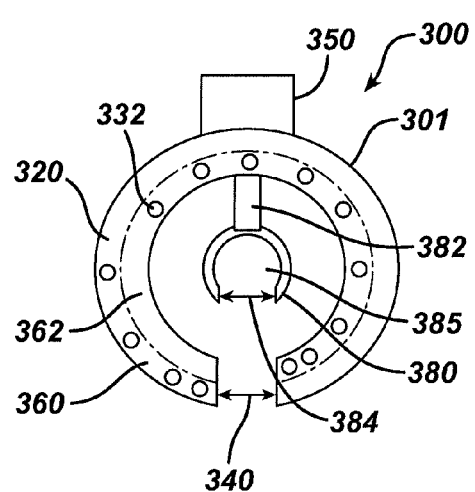

Referring to FIG. 8, in one embodiment, only the first component, e.g. either fibrinogen or thrombin, of a two part sealant is sprayed from top surface 320 and only the second component, e.g. either thrombin or fibrinogen is sprayed from bottom surface 322. As shown in FIG. 8A, in the top view of sealant delivery device 300 there are only nozzles 330 on top surface 320 to deliver the first component. As shown in FIG. 8B, in the bottom view of sealant delivery device 300 there are only nozzles 332 on bottom surface 322 to deliver the second component. The nozzles location and their respective delivery angles facilitate deposition of first component, such as fibrinogen onto one serosal surface and second component, such as thrombin onto another serosal surface. In this embodiment, the solutions are prevented from reacting with one another until the device 300 is removed and stapling occurs. Advantageously, there is more time to perform necessary preparations for stapling without the threat of premature reacting of the two part sealant, such as premature formation of fibrin.

Figure 9:
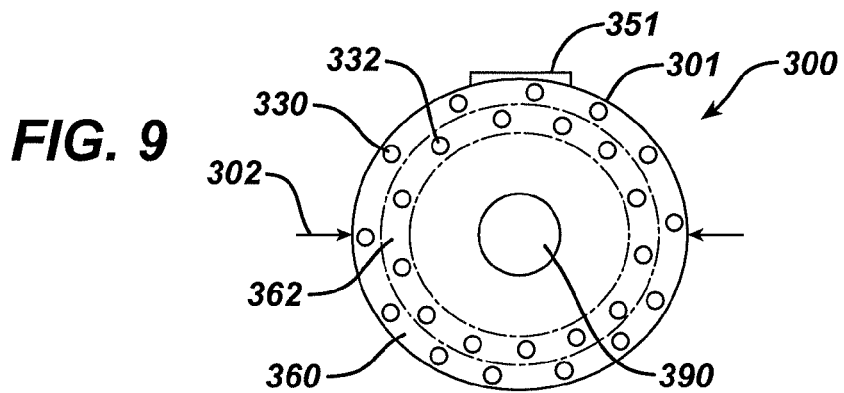
FIG. 9 shows schematic top view of an embodiment of the present invention.
Figure 10A:
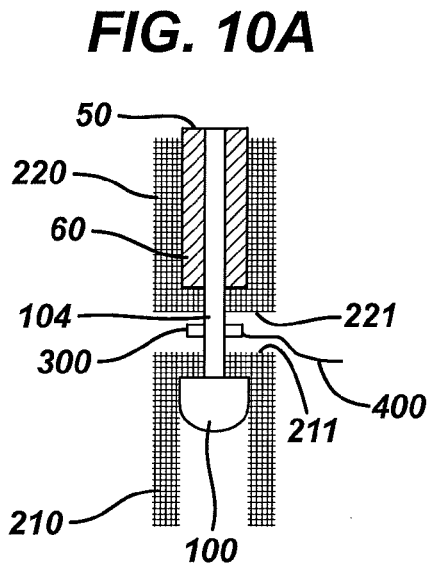
FIGS. 10A-10D show schematic cross-sectional view of an embodiment of the present invention in operation during anastomosis using the anastomotic stapler.
Figure 10B:
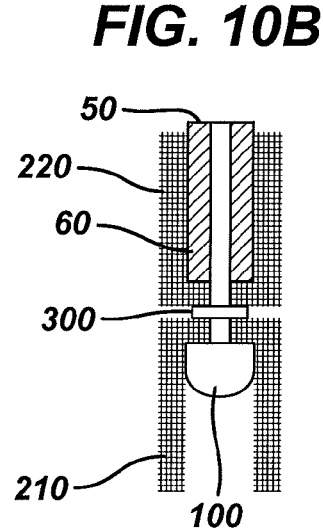
Figure 10C:
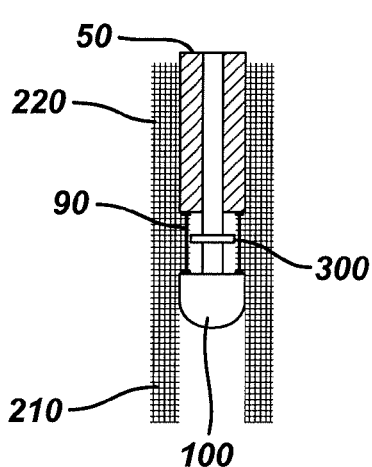
Figure 10D:
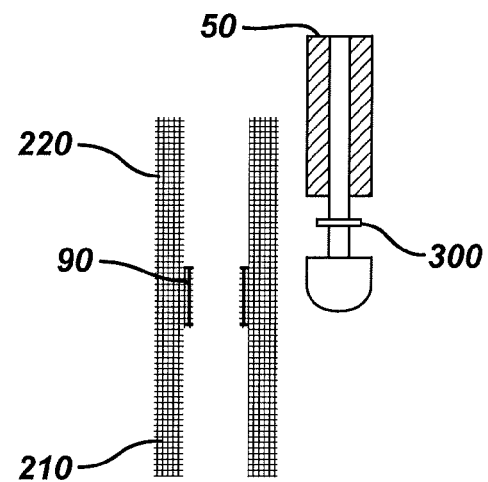

Referring now to FIG. 9, in one embodiment, sealant delivery device 300 is adapted to not being removed from shaft 104 before stapling, but only being disconnected from dual lumen cannula 400 (not shown) supplying two part sealant, such as fibrinogen and thrombin. In this embodiment, sealant delivery device 300 is affixed onto shaft 104 via a circular opening 390, and manifold has a low profile and is embedded into housing 301 forming a port 351. Diameter of circular opening 390 is substantially equal to or slightly greater than diameter of shaft 104 to ensure a good fit with possibility of slidable repositioning. In this embodiment, sealant delivery device 300 stays on shaft 104 during and after stapling and action of the circular cutter removing excess of the inverted bowel. Sealant delivery device 300 is removed together with surgical stapling instrument 50.

Referring now to FIG. 10, the operation of this embodiment during anastomosis is further illustrated. As shown in FIG. 10A, sealant delivery device 300 is connected to dual lumen cannula 400, dual lumen cannula 400 is used to deliver two part sealant to serosal surfaces 221 and 211, after which dual lumen cannula 400 is separated from port 351 and removed from the surgical site, and immediately thereafter anvil 100 is approximated to stapling head assembly 60, as shown in FIG. 10B. Advantageously, the thickness of sealant delivery device 300 is less than the thickness of layers of tissue being stapled, and the diameter 302 of sealant delivery device 300 is smaller than the cut performed by circular cutter (not shown) removing excess of the inverted bowel. As shown in FIG. 10C, sealant delivery device 300 is positioned between anvil 100 and stapling head assembly 60 after staples 90 are deployed (with the tissue of the inverted bowel removed by circular cutter not shown). As shown in FIG. 10D, sealant delivery device 300 stays attached to surgical stapling instrument 50 after surgical stapling instrument 50 is removed.

In certain embodiments, the diameter of the hollow housing 301 is from about 8 mm to about 40 mm, such as 15 mm or 25 mm. In certain embodiments, the diameter of the coupler opening 385 is from about 4 mm to about 15 mm, such as 5 mm or 7 mm. In certain embodiments, housing gap 340 has the dimensions from zero to about 15 mm, more preferably from 1 mm to about 12 mm, such as 4 mm, 5 mm, or 6 mm. In certain embodiments, coupler gap 384 has the dimensions from zero to about 10 mm, more preferably from 1 mm to about 12 mm, such as 3 mm, 4 mm, or 5 mm. In certain embodiments, thickness of the hollow housing 301 is from about 1 mm to about 5 mm, more preferably 2 mm to 3 mm, such as 2.5 mm. In certain embodiments, the width of arms 310 and 312 is from about 2 mm to about 8 mm, such as 3 mm or 5 mm. In certain embodiments, channels 360 and 362 have cross-sectional area of from about 0.25 mm$^2$ to about 10 mm$^2$, such as 0.5 mm$^2$, 1 mm$^2$ or 2 mm$^2$. In certain embodiments, nozzles 330 and 332 have diameter of from 0.1 mm to 1 mm, such as 0.3 mm, 0.5 mm. In certain embodiments, there are 5 to 20 nozzles 330 and 5 to 20 nozzles 332 on top surface 320 and the same amount of nozzles on bottom surface 322. In some embodiments there are 10 nozzles 330 and 10 nozzles 332 on top surface 320 and same amount of nozzles on bottom surface 322. In some embodiments there are 10 or more nozzles 330 on top surface 320 and 10 or more nozzles 332 on bottom surface 322, with no nozzles 332 on top surface 320 and no nozzles 330 on bottom surface 322. In some embodiments nozzles 330 and 332 are spaced equidistantly from each other in a circumferential arrangement on the periphery of hollow housing 301, with distance between neighboring nozzles of the same type being from 2 mm to about 6 mm, such as 4 mm.

Advantageously, different sized and configurations of sealant delivery device 300 can be utilized with the same type of circular anastomosis surgical stapling instrument 50, thus providing the surgeon with the possibility to accommodate different anatomical dimensions and individual requirements for performing anastomosis.

Sealant delivery device 300 can be made by machining, injection molding, additive or rapid prototyping techniques, such as 3D printing, and other methods known in the art. The device materials are typically biocompatible polymeric materials, such as polyethylene, PET, polypropylene, Teflon or PTFE, silicone, or biocompatible metal such as stainless steel or nitinol, and other materials known in the art. Nozzles 330 and 332 can be made by any known techniques, such as drilling, laser machining, or molding apertures in place.

Two-part sealant is preferably a biologically compatible sealant, such as synthetic sealant or biologics-based sealant, such as for example fibrin glue which comprises fibrinogen, thrombin, and optionally any other additives such as stabilizers, thickeners, growth factors, fibrinolytic inhibitors etc. as known in the art. Thickeners can be added to fibrinogen and/or thrombin solutions to increase viscosity. The increased viscosity will reduce any run-off of the solutions from the serosal surfaces and allow for better targeting. Alternatively very low temperature of the solution (such as 5° C.) can be used which makes it both viscous and slower to react. Fibrinogen and thrombin solutions can be used in a variety of mixing ratios, such as 1:1 fibrinogen: thrombin or 2:1 or 5:1 or 10:1 or 20:1 or 50:1. Having lower concentration of thrombin can be advantageous to reduce curing or reaction rate so that most of reaction will occur after the firing of the stapling instrument 50. Examples of two part sealant include, EVICEL® Fibrin Sealant (Human), available from Johnson & Johnson Wound Management Worldwide, a division of Ethicon, Inc., Somerville, N.J.; TISSEEL Fibrin sealant, Baxter Healthcare Corporation, Westlake Village, Calif.; other sources of fibrin sealant such as animal sourced or recombinant fibrinogen and/or thrombin.

Example 1

A sealant delivery device according to embodiments shown in FIGS. 4A-B was made of polymeric material by using rapid prototyping techniques, with diameter of the hollow housing 301 being 19 mm; diameter of the coupler opening 385 being 6 mm; size of the housing gap 340 being 5.5 mm; size of the coupler gap 384 being 3.5 mm; the width of arms 310 and 312 being 3.5 mm; the thickness of the hollow housing 301 being 2.5 mm. The device had ten nozzles 330 and eleven nozzles 332 on top surface 320 and the same amount of nozzles on the bottom surface 322. The sealant delivery device was then tested by affixing it to a circular surgical stapling instrument and supplying EVICEL® Fibrin Sealant (Human), available from Johnson & Johnson Wound Management Worldwide, a division of Ethicon, Inc., Somerville, N.J. to the sealant delivery device via a two lumen cannula 400, resulting in spraying of the two part sealant in direction perpendicular to top surface 320 and bottom surface 322 and towards model serosal surfaces. The connection was made in a way that ensured coupling of lumens to ports on the device. It was observed that the sealant delivery device did not clog and successfully ejected and sprayed components of two part sealant, which formed fibrin on the model serosal surfaces.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

The invention claimed is:

1. A circular anastomosis surgical stapling instrument, comprising:
  a shaft, an anvil, a stapling head, and a device for applying adhesive components or sealant components to anastomosis site;
  the device comprising:
    a hollow housing with a plurality of exit openings and
    a coupler adapted to mount the device to the shaft of the circular anastomosis surgical stapling instrument;
    wherein the hollow housing having a top surface and an opposing bottom surface with at least two separate channels within said housing;
    the plurality of exit openings comprise a plurality of nozzles disposed circumferentially on the to surface and on the bottom surface with the plurality of nozzles in fluid communication with the channels;
    a manifold connector attached to the hollow housing, the manifold connector being in fluid communication with the channels and adapted to be connected to a dual lumen cannula for supplying the adhesive components or the sealant components;
    wherein said coupler is adapted to mount the device to the shaft between the anvil and the stapling head of the circular anastomosis surgical stapling instrument;
    wherein said channels comprise a first channel and a second channel;
  wherein said nozzles comprise a first set of nozzles in fluid communication with the first channel and a second set of nozzles in fluid communication with the second channel;
    wherein the hollow housing has a semicircular shape, with a housing gap dividing the hollow housing into two housing arms; and
    wherein the coupler has a semicircular opening having an inner diameter equal to a diameter of the shaft, and wherein the coupler is adapted to be snapped onto the shaft.

2. The circular anastomosis surgical stapling instrument of claim 1, wherein the coupler comprises two coupler arms separated by a coupler gap, wherein the coupler gap is smaller than the diameter of the shaft.

3. The circular anastomosis surgical stapling instrument of claim 2, wherein said housing gap has dimensions equal to or larger than the diameter of the shaft.

4. The circular anastomosis surgical stapling instrument of claim 2, wherein said housing gap is smaller than the diameter of the shaft and wherein the housing arms are flexibly or hingeably adapted to accept the shaft.

5. The circular anastomosis surgical stapling instrument of claim 1, wherein the coupler comprises a radial cut having width equal to a diameter of the shaft, said radial cut terminating in a center of the housing as a semicircular opening having a diameter equal to the diameter of the shaft, wherein one or more locking elements are positioned within the radial cut, said locking elements enabling the device to be snapped onto the shaft.

6. The circular anastomosis surgical stapling instrument of claim 1, wherein the first set of nozzles is disposed on the top surface and the second set of nozzles is disposed on the bottom surface.

7. The circular anastomosis surgical stapling instrument of claim 1, wherein the nozzles are adapted to eject the adhesive components or the sealant components perpendicularly to the top surface and to the bottom surface.

8. The circular anastomosis surgical stapling instrument of claim 1, wherein the nozzles are adapted to eject the adhesive components or the sealant components angularly to the top surface and to the bottom surface.

9. The circular anastomosis surgical stapling instrument of claim 1, wherein at least some nozzles are adapted to eject the adhesive components or the sealant components perpendicularly to the top surface and to the bottom surface, and at least other nozzles are adapted to eject the adhesive components or the sealant components angularly to the top surface and to the bottom surface.

10. The circular anastomosis surgical stapling instrument of claim 1, wherein the nozzles are positioned circumferentially on the housing, with the nozzle for one component of the adhesive or the sealant followed by the nozzle for another component of the adhesive or the sealant.

11. The circular anastomosis surgical stapling instrument of claim 1, further comprising a flexible tether connected to the device, said tether adapted to facilitate the device removal from said shaft.

12. The circular anastomosis surgical stapling instrument of claim 1, wherein the nozzles are positioned with uniform density along the two housing arms.

13. The circular anastomosis surgical stapling instrument of claim 1, wherein the nozzles are positioned with uniform density along the two housing arms and wherein the nozzles are positioned with higher density close to the housing gap.

14. The circular anastomosis surgical stapling instrument of claim 1, wherein the adhesive components or the sealant components comprises a fibrin sealant.

15. A method of performing anastomosis, comprising:
  preparing the anastomosis site for performing anastomotic stapling;
  connecting the manifold connector of the device of the circular anastomosis surgical stapling instrument of claim 1 to a dual lumen cannula;
  coupling the device to the shaft of the circular anastomosis surgical stapling instrument between the anvil and the stapling head of the circular anastomosis surgical stapling instrument;
  connecting the dual lumen cannula to a source of a two-part sealant;
  delivering the two-part sealant from the source via the dual lumen cannula into the device;
  ejecting the two-part sealant from the nozzles;
  depositing the two-part sealant onto the anastomosis site;
  removing the device from the shaft;
  firing the circular anastomosis surgical stapling instrument delivering staples and performing anastomosis.

* * * * *